United States Patent [19]
Wells et al.

[11] Patent Number: 5,120,532
[45] Date of Patent: * Jun. 9, 1992

[54] HAIR STYLING SHAMPOOS

[75] Inventors: Robert L. Wells, Cincinnati, Ohio; Bonnie T. King, Alexandria, Ky.; Michael A. Snyder; Donald H. Frey, both of Cincinnati, Ohio

[73] Assignee: The Procter & Gamble Company, Cincinnati, Ohio

[*] Notice: The portion of the term of this patent subsequent to Apr. 14, 2009 has been disclaimed.

[21] Appl. No.: 506,407

[22] Filed: Apr. 6, 1990

[51] Int. Cl.$^5$ .............................................. A61K 0/75
[52] U.S. Cl. ........................................ 424/70; 424/71
[58] Field of Search ................ 424/70,71,78,DIG. 2; 252/DIG. 13

[56] References Cited

U.S. PATENT DOCUMENTS

| | | | |
|---|---|---|---|
| 2,816,882 | 12/1957 | Schiller | 526/307.7 |
| 2,834,763 | 5/1958 | Halpern et al. | 526/245 |
| 2,996,471 | 8/1961 | Reiter | 424/47 |
| 3,072,536 | 1/1963 | Pye | 167/85 |
| 3,222,329 | 12/1965 | Grosser et al. | 260/80.5 |
| 3,405,084 | 10/1968 | Bohac | 260/29.6 |
| 3,445,566 | 5/1969 | Skoultchi | 424/17 |
| 3,577,517 | 5/1971 | Kubot et al. | 424/47 |
| 3,743,715 | 7/1973 | Viout et al. | 424/47 |
| 3,810,977 | 5/1974 | Levine | 424/47 |
| 3,907,984 | 9/1975 | Calvert et al. | 424/47 |
| 3,927,199 | 12/1975 | Micchelli | 424/47 |
| 3,936,513 | 2/1976 | Lorenz et al. | 525/379 |
| 4,012,501 | 3/1977 | Farber | 424/47 |
| 4,030,512 | 6/1977 | Papantoniou et al. | 132/7 |
| 4,067,839 | 1/1978 | Schultz | 526/916 |
| 4,151,333 | 4/1979 | Lenke et al. | 526/307.7 |
| 4,165,367 | 8/1979 | Chakrabarti | 424/47 |
| 4,192,861 | 3/1980 | Micchelli | 424/47 |
| 4,196,190 | 4/1980 | Gehman et al. | 424/47 |
| 4,223,009 | 9/1980 | Chakrabarti | 424/47 |
| 4,272,511 | 6/1981 | Papantoniou et al. | 424/47 |
| 4,283,384 | 8/1981 | Jacquet et al. | 424/47 |
| 4,374,825 | 2/1983 | Bolich, Jr. et al. | 424/70 |
| 4,387,090 | 6/1983 | Bolich, Jr. | 424/70 |
| 4,388,436 | 6/1983 | Chen | 524/553 |
| 4,548,990 | 10/1985 | Mueller et al. | 526/320 |
| 4,798,721 | 1/1989 | Yahagi et al. | 424/70 |
| 4,842,852 | 6/1989 | Nowak | 424/71 |
| 4,886,660 | 12/1989 | Patel | 424/70 |
| 4,963,348 | 10/1990 | Bolich, Jr. et al. | 424/DIG. 2 |

FOREIGN PATENT DOCUMENTS

| | | |
|---|---|---|
| 116207 | 8/1984 | European Pat. Off. . |
| 1195050 | 6/1965 | Fed. Rep. of Germany . |
| 60-229909 | 11/1985 | Japan . |
| 60-250015 | 12/1985 | Japan . |
| 0833995 | 5/1981 | U.S.S.R. . |
| 467402 | 6/1937 | United Kingdom . |
| 764409 | 12/1956 | United Kingdom . |
| 2155788 | 10/1985 | United Kingdom . |

OTHER PUBLICATIONS

Technical Leaflet—Luviskol VA Grades—Dec./1984.
Technical Leaflet—Luviskol VAP Grades—Feb./84.
Encyclopedia of Polymer Science & Engineering, vol. 7, pp. 531–544, John Wiley and Sons, 1987.
Copending Application Ser. No. 285,137, Torgerson, filed Dec. 16, 1988.

*Primary Examiner*—Thurman K. Page
*Attorney, Agent, or Firm*—Leonard W. Lewis; Steven J. Goldstein

[57] ABSTRACT

The present invention relates to hair shampoo compositions comprising from about 5% to about 30% of a surfactant, from about 0.2% to about 20% of certain hair styling polymers, and from about 0.2% to about 20% of a solvent for said hair styling polymer. These compositions provide hair cleaning and styling benefits from a single product. Preferred compositions of the present invention additionally comprise from about 0.01% to about 10% of a silicone hair conditioning agent. These compositions provide hair conditioning, cleaning and styling benefits from a single product.

41 Claims, No Drawings

HAIR STYLING SHAMPOOS

TECHNICAL FIELD

The present invention relates to hair shampoo compositions which provide not only hair cleaning benefits, but also hair styling benefits. These are achieved by incorporating certain hair styling polymers and solvents for said polymers in a shampoo base. In addition, hair conditioning agents can be included in the compositions to provide hair conditioning, cleaning and style hold benefits from a single product.

BACKGROUND OF THE INVENTION

In washing, drying and styling one's hair several end results are desired. Firstly, and most obviously, one desires that the hair be thoroughly cleaned. Most desirable is a hair care process which maintains the look and feel of clean hair between hair washings. Also in the cleaning and styling process, one desires hair conditioning providing ease of combing, relief from static electricity, manageability, and soft hair feel. Generally, these benefits are provided by a separate hair conditioning product.

Finally, one desires a hair care process or product that provides hair styling benefits, especially hair style achievement and hold. The desire to have hair retain a particular shape is widely held. Such style retention is generally accomplished by either of two routes: permanent chemical alteration or temporary alteration of hair style/shape. A temporary alteration is one which can be removed by water or by shampooing. Temporary style alteration has generally been accomplished by means of the application of a third separate composition or compositions to dampened hair after shampooing and/or conditioning. The materials used to provide setting benefits have generally been resins or gums and have been applied in the form of mousses, gels, lotions, or sprays. This approach presents several significant drawbacks to the user. It requires a separate step following shampooing and conditioning to apply the styling composition. In addition, since the style hold is provided by resin materials which set-up on the hair, the hair tends to feel sticky or stiff after application and it is difficult to restyle the hair without further application of the styling composition. It has now been discovered that two separate hair care benefits, i.e., cleaning and styling benefits, can be provided by a single hair care product. The present invention relates to hair shampoo compositions which comprise surfactants and hair styling agents. Shampooing with these products provides hair cleaning and styling benefits. It has also been discovered that if a silicone hair conditioning agent is added to the aforementioned product, hair conditioning, cleaning and styling benefits can be achieved from a single hair care product. It has also been discovered that the aforementioned products provide some degree of restyling benefit to the hair. It is an object of the present invention to formulate hair care compositions which provide effective hair cleaning, styling, and preferably conditioning properties.

It is also an object of the present invention to formulate hair care compositions which provide cleaning, styling, and preferably, conditioning benefits from a single composition.

It is a further object of the present invention to formulate hair care compositions which provide good style retention benefits without leaving hair with a stiff or sticky/tacky feel. It is a further object of the present invention to provide an improved method for cleaning, styling, and preferably, conditioning, hair.

These and other objects will become readily apparent from the detailed description which follows.

SUMMARY OF THE INVENTION

The present invention relates to shampoo compositions comprising:
a. from about 5% to about 30% of a surfactant;
b. from about 0.2% to about 20% of a hair styling polymer comprising:
A. from 0% to about 30% of a polymerizable hydrophilic monomer ($M_A$), or mixtures thereof; and
B. from about 70% to about 100% of a polymerizable hydrophobic monomer ($M_B$), or mixtures thereof;
said polymer having a molecular weight of from about 5,000 to about 1,000,000, a Tg of greater than about $-20°$ C., and a solubility parameter, $\delta$, of from about 8.5 to about 12.0; and
c. from about 0.2% to about 20% of a solvent which will solubilize said polymer, said solvent having a boiling point of less than or equal to about 300° C., and a solubility parameter, $\delta_s$, of from about 7 to about 12.5; and wherein the polymer and solvent are present in the hair shampoo as a dispersed fluid phase; wherein the ratio of polymer to solvent is from about 20:80 to about 80:20; and wherein the percent hydrophilic monomer, $M_A$, if present, is as follows:

$$\%M_A = (\delta_s - 6.7) \times 5.56 \pm 10.$$

DETAILED DESCRIPTION OF THE INVENTION

The essential, as well as the optional, components of the present invention are described below.

Styling Agents

The shampoo compositions of the present invention contain, as an essential component, a hair styling polymer. It is this component that provides hair styling benefits to the user.

A wide variety of hair setting polymers are known for use as styling agents. Many polymers said to be useful in hair styling products are multi-component polymers which combine three, four and even more different monomers into the polymer chains. Frequently, one of the monomer components is vinyl pyrrolidone. Examples of such complex polymer systems are found in U.S. Pat. No. 3,222,329 to Grosser et al., issued Dec. 7, 1965; U.S. Pat. No. 3,577,517 to Kubot et al., issued May 4, 1971; U.S. Pat. No. 4,012,501 to Farber, issued Mar. 15, 1977; U.S. Pat. No. 4,272,511 to Papantoniou and Mondet, issued Jun. 9, 1981; and U.S. Pat. No. 4,196,190, to Gehman et al., issued Apr. 1, 1980.

Other polymers said to be useful for hair styling compositions have been disclosed, such as block polymers. Examples of such block polymer systems are found in U.S. Pat. No. 3,907,984 to Calvert et al., issued Sep. 23, 1975; U.S. Pat. No. 4,030,512 to Papantoniou et al., issued Jun. 21, 1977; and U.S. Pat. No. 4,283,384 to Jacquet et al., issued Aug. 11, 1981.

It has been found that styling polymers having water-solubilities within a certain range provide optimum hair styling benefits when delivered from a shampoo. The styling polymers of
the present invention are of relatively low water-solubility. More specifically, these polymers have a solubility parameter, δ, of between about 8.5 and about 12.0 (δ units equal $(cal/cm^3)^{\frac{1}{2}}$), preferably from about 9.5 to about 11.5, most preferably from about 11 to about 11.5.

The solubility parameter is defined in the Polymer Handbook 3rd Ed. (John Wiley and Sons, New York), J. Brandrup and E.H. Immergut, Chapter VII, pp. 519-559, as the square root of the cohesive energy density and describes the attractive strength between molecules of the material. Solubility parameters may be determined by direct measurement, correlations with other physical properties, or indirect calculation. The solubility parameters of the present polymers were determined by indirect calculations of group contributions as described in section 2.3 on p. 524-526 of the cited reference.

It has been found that styling polymers having water solubilities within this range can be dispersed with the polymer solvent, as described infra. in shampoo compositions as a dispersed fluid phase. Formulation in this way has been shown to provide maximum deposition of styling polymer out of the shampoo composition and onto hair. Styling polymers having solubility parameters at the upper end of this range would be soluble by themselves in the present shampoo compositions. It has now been found that when these polymers are combined with the polymer solvents of the present invention (as defined infra) and then dispersed in the shampoo composition, they remain in the composition as a dispersed fluid phase. Polymers having solubility parameters greater than about 12.0 will themselves be solubilized in the shampoo composition (even when they are premixed with the present polymer solvents) preventing optimum deposition of polymer on hair. Styling polymers having solubility parameters lower than about 8.5 will not deposit effectively from the shampoo.

The present styling polymers must comprise at least one polymerizable hydrophobic monomer. The polymer may be a homopolymer or a copolymer of hydrophobic monomers. Alternatively, the present styling polymers may be a copolymer of a hydrophilic monomer and a hydrophobic monomer, or mixtures thereof. Hence, the present hair styling polymers comprise from 0% to about 30% of a polymerizable hydrophilic monomer ($M_A$) or mixtures thereof, and from about 70% to about 100% of a polymerizable hydrophobic monomer ($M_B$), or mixtures thereof. Of course, if the styling polymer comprises both $M_A$ monomer and $M_B$ monomer, then the monomers must be copolymerizable with each other. If the polymer comprises a hydrophilic monomer, then the following relationship must hold true as well:

$$\% M_A = (\delta_s - 6.7) \times 5.56 \pm 10$$

wherein $M_A$ is the hydrophilic monomer and $\delta_s$ is the solubility parameter of the polymer solvent component (as described infra). (If % $M_A$ is calculated as less than zero, then no hydrophilic monomer is included in the copolymer). Preferably, the relationship is as follows:

$$\% M_A = (\delta_s - 6.7) \times 5.56 \pm 3.$$

Preferred hydrophilic monomers of the present styling polymers include acrylic acid, methacrylic acid, N,N-dimethylacrylamide, dimethylaminoethyl methacrylate, methacrylamide, N-t-butyl acrylamide, maleic acid, maleic anhydride and its half esters, crotonic acid, itaconic acid, acrylamide, acrylate alcohols, hydroxyethyl methacrylate, vinyl pyrrolidone, vinyl ethers (such as methyl vinyl ether), maleimides, vinyl pyridine, vinyl imidazole, other polar vinyl heterocyclics, styrene sulfonate, allyl alcohol, vinyl alcohol (produced by the hydrolysis of vinyl acetate after polymerization), vinyl caprolactam, and mixtures thereof.

Preferred hydrophobic monomers include acrylic or methacrylic acid esters of $C_1$-$C_{18}$ a alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, neodecanol, 2-ethyl-butanol, 3-heptanol, benzyl alcohol, 2-octanol, 6-methyl-1-heptanol, 2-ethyl-1-hexanol, 3,5-dimethyl-1-hexanol, 3,5,5-trimethyl1-hexanol, 1-decanol, and the like, the alcohols having from about 1-18 carbon atoms with the average number of carbon atoms being from about 4-12; styrene; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene; methoxy ethyl methacrylate; and mixtures thereof.

Optimum performance of the present hair styling polymers in terms of style hold has been found when the weight average molecular weight of the styling polymer is between about 5,000 and about 1,000,000, preferably between about 10,000 and about 100,000, and the glass transition temperature, Tg, (i.e., the temperature at which the polymer changes from a brittle vitreous state to a plastic state) of the styling polymer is greater than about $-20°$ C., preferably between about 0° C. and about 80° C., and most preferably between about 20° C. and about 60° C.

Specific styling polymers of the present invention which have been found to provide the desired deposition/styling benefits out of a shampoo system are as follows: vinyl pyrrolidone/vinyl acetate copolymers (at ratios of up to about 30%, by weight, vinyl pyrrolidone); vinyl acetate homopolymer; t-butyl acrylate homopolymer; t-butyl styrene/ ethyl hexyl methacrylate copolymer (50/50, by weight); dimethyl acrylamide/ t-butyl acrylate/ethyl hexyl methacrylate copolymer (10/45/45); ethylene/vinyl acetate copolymer (12.5/87.5); allyl alcohol/styrene copolymer (19/81); vinyl chloride/vinyl acetate copolymer (83/17 and lower); vinyl pyrrolidone/vinyl acetate/butyl acrylate copolymer (10/78/12 and 10/70/20); vinyl pyrrolidone/ vinyl acetate/butyl acrylate/styrene sulfonate copolymer (10/70/15/5); vinyl pyrrolidone/vinyl propionate copolymer (5/95); vinyl caprolactam/vinyl acetate copolymer (5/95); and styling resins sold under the trade names Ultrahold CA 8 ® by Ciba Geigy (ethyl acrylate/ acrylic acid/N-t-butyl acrylamide copolymer), Resyn 28-1310 ® by National Starch and Luviset CA 66 ® by BASF (vinyl acetate/crotonic acid copolymer 90/10); Luviset CAP ® by BASF (vinyl acetate/vinyl propionate/crotonic acid 50/40/10); and Resyn 28-2930 ® by National Starch (vinyl acetate/vinyl neodecanoate/crotonic acid copolymer). The most preferred copolymers for use in the present invention are copolymers of vinyl pyrrolidone and vinyl acetate containing at most 30% vinyl pyrrolidone, and preferably containing the monomers at a weight ratio of about 5/95.

The polymer styling agent is present in the compositions of the present invention at a level of from about 0.2% to about 20%, preferably at a level of from about 2% to about 6%. At levels below about 0.2% styling polymer, the present hair style hold benefits cannot be achieved; at levels above about 20% styling polymer, interference with shampoo in-use characteristics may occur.

The styling polymers of the present invention formulated in the present shampoo compositions provide hair styling benefits. Such benefits include ease of style achievement and style maintenance. The present compositions also provide some degree of restyling benefits. That is, after the hair is shampooed with the present compositions and styled, the hair "remembers" the style after being subjected to a force, such as combing, brushing or simply flattening of the hair.

Polymer Solvent

A second essential component of the present shampoo compositions is a solvent or diluent for the styling polymer. The solvent is necessary for dilution of the polymer so that it can be dispersed in the shampoo composition. The solvent also aids in delivering style achievement by making polymer deposited on the hair more tacky through the hair drying and styling process. The polymer solvent must have a low solubility in water, comparable with the water solubility of the polymer. The particular polymer chosen for use in the present shampoo compositions must be soluble in the particular solvent utilized. This enables the dispersion of the polymer/solvent mixture as a dispersed fluid phase in the shampoo composition and maintenance of that dispersed second phase. Hence, the polymer solvents of the present invention have a solubility parameter, $\delta_s$, of between about 7 and about 12.5, preferably between about 8 and about 10. The solubility parameters of solvents are usually determined by direct measurement. Values for $\delta_s$ for the solvents of the present invention were taken from Table 3.1 and 3.2 in the Polymer Handbook reference cited above. The upper end of this solubility range covers solvent materials which, if dispersed in the shampoo base alone, would be soluble. However, it has been found that when these solvents are premixed with the polymers of the present invention, prior to dispersion in the shampoo composition, they will remain in the polymer phase, i.e., unsolubilized in the shampoo base.

The polymer solvent must also be volatile. Upon deposition of the polymer/solvent mixture on the hair, the solvent is volatilized leaving only the styling polymer on the hair, thus providing the maximum styling benefits. Generally, the polymer solvents of the present invention have a boiling point of less than or equal to about 300° C.

Additionally, the polymer solvent must not interact with the polymer styling agent in such a way that would substantially reduce the ability of the polymer to provide styling benefits to hair under ordinary use situations. The solvents must, of course, be of sufficiently high purity and sufficiently low toxicity to render them suitable for administration to human hair.

Specific polymer solvent materials that have been found to be useful in the present invention include isopropanol, butyl alcohol, amyl alcohol, phenyl ethanol, benzyl alcohol, phenyl propanol, ethyl butyrate, isopropyl butyrate, diethyl phthalate, phenyl ethyl dimethyl carbinol, ethyl-6-acetoxyhexanoate, and methyl(2-pentanyl-3-oxy)cyclopentylacetate, and mixtures thereof. Preferred solvents for use herein are diethyl phthalate, phenyl ethyl dimethyl carbinol, ethyl-6-acetoxyhexanoate, and mixtures thereof.

The amount of solvent to be used in the present shampoo compositions is an amount sufficient to solubilize the polymer and disperse it as a separate fluid phase in the shampoo composition. Generally, from about 0.2% to about 20%, preferably from about 2% to about 6%, polymer solvent is used. At levels below about 0.2% solvent, the polymer cannot be sufficiently diluted; at levels above about 20% solvent, shampoo in-use characteristics may be negatively affected. The ratio of polymer to solvent in the present composition is from about 10:90 to about 80:20, preferably from about 40:60 to about 60:40.

European Patent Publications 0320218, published Jun. 14, 1989, and 0323715, published Jul. 12, 1989, disclose certain hair styling polymers and solvents therefor, useful in hair care compositions, including shampoos and rinse-off hair conditioners. EPO Patent Publication 0323715 teaches polymer and solvent systems having very low water solubilities (polymer is less than 0.1% soluble in water, diluent is less than 0.2% soluble in water) which are dispersed as a separate fluid phase in hair care compositions. Polymer/solvent systems having such low water solubilities have been found to interfere with the present shampoo in-use characteristics, namely lathering.

Cleaning Agent

Another essential component of the present shampoo compositions is a surfactant. The surfactant comprises from about 5% to about 30%, preferably from about 12% to about 25%, of the shampoo composition. A wide variety of surfactant materials may be utilized including anionic, nonionic, cationic, zwitterionic and amphoteric surfactants.

Synthetic anionic detergents useful herein include alkyl and alkyl ether sulfates. These materials have the respective formulae $ROSO_3M$ and $RO(C_2H_4O)_xSO_3M$, wherein R is alkyl or alkenyl of from about 8 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having from about 8 to about 20 carbon atoms. Preferably, R has from about 12 to about 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with about 1 to about 10, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the present invention are sodium coconut alkyl triethylene glycol ether sulfate; sodium tallow alkyl triethylene glycol ether sulfate; and sodium tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 4 moles of ethylene oxide. Such a mixture also comprises from about 0 to about 20% by weight $C_{12-13}$ compounds; from about 60 to about 100% by weight of $C_{14-15-16}$ compounds, from about 0 to about 20% by weight of $C_{17-18-19}$ compounds; from about 3 to about 30% by weight of compounds having a degree of ethoxylation of 0; from about 45 to about 90% by weight of compounds having a degree of ethoxylation of from about 1 to about 4; from about 10 to about 25% by weight of compounds having a degree of ethoxylation of from about 4 to about 8; and from about 0.1 to about 15% by weight of compounds having a degree of ethoxylation greater than about 8.

Another suitable class of anionic surfactants are the watersoluble salts of the organic, sulfuric acid reaction products of the general formula:

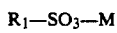

$$R_1-SO_3-M$$

wherein $R_1$ is chosen from the group consisting of a straight or branched chain, saturated aliphatic hydrocarbon radical having from about 8 to about 24, preferably about 12 to about 18, carbon atoms; and M is a cation. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., S03, $H_2SO_4$, oleum, obtained according to known sulfonation methods, including bleaching and hydrolysis. Preferred are alkali metal and ammonium sulfonated $C_{12-18}$ n-paraffins.

Additional examples of anionic synthetic surfactants which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other anionic synthetic surfactants of this variety are set forth in U.S. Pat. Nos. 2,486,921; 2,486,922; and 2,396,278.

Still other anionic synthetic surfactants include the class designated as succinamates. This class includes such surface active agents as disodium N-octadecylsulfosuccinamate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Other suitable anionic surfactants utilizable herein are olefin sulfonates having about 12 to about 24 carbon atoms. The term "olefin sulfonates" is used herein to mean compounds which can be produced by the sulfonation of α-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The α-olefins from which the olefin sulfonates are derived are mono-olefins having about 12 to about 24 carbon atoms, preferably about 14 to about 16 carbon atoms. Preferably, they are straight chain olefins. Examples of suitable 1-olefins include 1-dodecene; 1-tetradecene; 1-hexadecene; 1-octadecene; 1-eicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion f reactants, the nature of the starting olefins and impurities in the olefin stock and side reactions during the sulfonation process.

A specific α-olefin sulfonate mixture of the above type is described more fully in the U.S. Pat. No. 3,332,880, Pflaumer and Kessler, issued Jul. 25, 1967, incorporated herein by reference.

Another class of anionic organic surfactants are the β-alkyloxy alkane sulfonates. These compounds have the following formula:

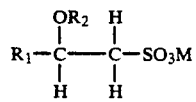

where $R_1$ is a straight chain alkyl group having from about 6 to about 20 carbon atoms, $R_2$ is a lower alkyl group having from about 1 (preferred) to about 3 carbon atoms, and M is a water-soluble cation as hereinbefore described.

Specific examples of β-alkyloxy-alkane-1-sulfonates, or alternatively 2-alkyloxy-alkane-1-sulfonates, having low hardness (calcium ion) sensitivity useful herein include: potassium-β-methoxydecanesulfonate, sodium 2-methoxy-tridecanesulfonate, potassium 2-ethoxytetradecylsulfonate, sodium 2-isopropoxyhexadecylsulfonate, lithium 2-t-butoxytetradecyl-sulfonate, sodium β-methoxyoctadecylsulfonate, and ammonium β-n-propoxydodecylsulfonate.

Many additional nonsoap synthetic anionic surfactants are described in *McCutcheon's, Emulsifiers and Detergents,* 1989 *Annual,* published by M. C. Publishing Co., which is incorporated herein by reference. Also U.S. Pat. No. 3,929,678, Laughlin et al., issued Dec. 30, 1975, discloses many other anionic as well as other surfactant types and is incorporated herein by reference.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to about 12 carbon atoms in either a straight chain or branched chain configuration, with ethylene oxide, the said ethylene oxide being present in amounts equal to from about 10 to about 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of about 2,500 to about 3,000, are satisfactory.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

$$R_1R_2R_3N \rightarrow O$$

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyl-dodecylamine oxide, oleyl-di(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

5. Long chain tertiary phosphine oxides corresponding to the following general formula:

$$RR'R''P \rightarrow O$$

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R'' are each alkyl or monohydroxyalkyl groups containing from about 1 to about 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide. 3,6,9,-trioxaoctadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleydimethylphosphine oxide, 2-hydroxydodecyldimethylphosphine oxide.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

7. Polyalkylene oxide modified dimethylpolysiloxanes, also known as dimethicone copolyols. These materials include the polyalkylene oxide modified dimethylpolysiloxanes of the following formulae:

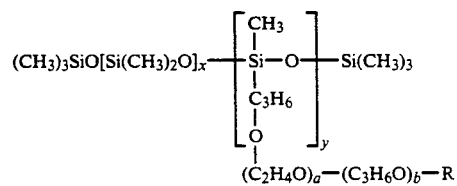

and

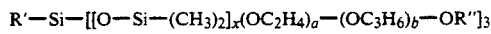

wherein R is hydrogen, an alkyl group having from 1 to about 12 carbon atoms, an alkoxy group having from 1 to about 6 carbon atoms or a hydroxyl group; R' and R'' are alkyl groups having from 1 to about 12 carbon atoms; x is an integer of from 1 to 100, preferably from 20 to 30; y is an integer of 1 to 20, preferably from 2 to 10; and a and b are integers of from 0 to 50, preferably from 20 to 30.

Dimethicone copolyols among those useful herein are disclosed in the following patent documents, all incorporated by reference herein: U.S. Pat. No. 4,122,029, Gee, et al., issued Oct. 24, 1978; U.S. Pat. No. 4,265,878, Keil, issued May 5, 1981; and U.S. Pat. No. 4,421,769, Dixon et al., issued Dec. 20, 1983. Commercially available dimethicone copolyols, useful herein, include Silwet Surface Active Copolymers (manufactured by the Union Carbide Corporation); Dow Corning Silicone Surfactants (manufactured by the Dow Corning Corporation); Silicone Copolymer F-754 (manufactured by SWS Silicones Corp.); and Rhodorsil 70646 Fluid (manufactured by Rhone Poulenc, Inc.).

Cationic surfactants useful in compositions of the present invention contain amino or quaternary ammonium hydrophilic moieties which are positively charged when dissolved in the aqueous composition of the present invention. Cationic surfactants among those useful herein are disclosed in the following documents, all incorporated by reference herein: M.C. Publishing Co., McCutcheon's, Detergents & Emulsifiers, (North American edition 1989); Schwartz, et al., Surface Active Agents, Their Chemistry and Technology. New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983. If included in the compositions of the present invention, the cationic surfactant must not interfere with the in-use performance and end-benefits of the shampoo. Generally it will be present at a level of from about 0.05% to about 5%.

Among the quaternary ammonium-containing cationic surfactant materials useful herein are those of the general formula:

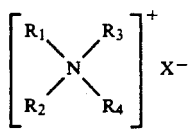

wherein $R_1$–$R_4$ are independently an aliphatic group of from about 1 to about 22 carbon atoms, or an aromatic, alkoxy, polyoxyalkylene, alkylamido, hydroxyalkyl, aryl or alkylaryl group having from about 12 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups.

Other quaternary ammonium salts useful herein have the formula:

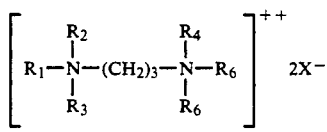

wherein $R_1$ is an aliphatic group having from about 16 to about 22 carbon atoms, $R_2$, $R_3$, $R_4$, $R_5$, and $R_6$ are selected from hydrogen and alkyl having from about 1 to about 4 carbon atoms, and X is an ion selected from halogen, acetate, phosphate, nitrate and alkyl sulfate radicals. Such quaternary ammonium salts include tallow propane diammonium dichloride.

Preferred quaternary ammonium salts include dialkyldimethylammonium chlorides and trialkyl methyl ammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms). Examples of quaternary ammonium salts useful in the present invention include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di-(hydrogenated tallow) dimethyl ammonium chloride and tricetyl methyl ammonium chloride are particularly preferred quaternary ammonium salts. These materials also provide anti-static benefits to the present shampoo compositions.

Salts of primary, secondary and tertiary fatty amines are also preferred cationic surfactant materials. The alkyl groups of such amines preferably have from about 12 to about 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, incorporated by reference herein.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

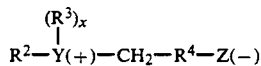

wherein $R_2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R_3$ is an alkyl or monohydroxyalkyl group containing about 1 to about 3 carbon atoms; X is 1 when Y is a sulfur atom, and 2 when Y is a nitrogen or phosphorus atom; $R_4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxy-propane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-(P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Other zwitterionics such as betaines are also useful in the present invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alphacarboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention. Preferred betaines for use in the present compositions are cocoamidopropyl betaine, cocobetaine, lauryl amidopropyl betaine, and oleyl betaine.

Examples of amphoteric surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

The above-mentioned surfactants can be used alone or in combination in the hair care compositions of the present invention. Preferred surfactants for use in the present shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, cocoamidopropyl betaine, cocobetaine, lauryl amido propyl betaine, oleyl betaine, and cocoamphocarboxyglycinate.

The most preferred shampoos of the present invention contain specific combinations of anionic surfactants, zwitterionic surfactants, and amphoteric surfactants. The preferred shampoos contain from about 2% to about 10% of a betaine, such as cocoamidopropyl betaine; from about 2% to about 16% of alkyl sulfates and alkyl ethoxylated sulfates, preferably from about 2% to about 6% alkyl sulfates and from 0% to about 14% of ethoxylated alkyl sulfates; and from 0% to about 8% of sarcosinates such as sodium lauroyl sarcosinate, with a total surfactant level of from about 15% to about 20%. The combination of betaine and alkyl sulfates and/or alkyl ethoxylated sulfates builds viscosity of the shampoo composition and increases lather upon use. The sarcosinate controls viscosity without decreasing lather and also aids in deposition of the styling agent. Thus, this surfactant combination, when used in a shampoo containing the preferred solvents of the present invention, gives optimum composition viscosity, in-use lather, and styling agent deposition.

Conditioning Agent

The shampoo compositions of the present invention also preferably comprise a hair conditioning agent. It is this agent that provides hair conditioning benefits such as ease of combing, soft hair feel, and manageability to the user. The resulting shampoo composition provides hair cleaning, styling and conditioning benefits in one product.

Cationic surfactants, as described previously, can be used to give some conditioning benefits in the present compositions. Similarly protein derivatives, such as hydrolyzed animal proteins, for example, Crotein SPA (Croda) or Lexeine X250 (Inolex) or Polypeptide LSN (Stephan), can be used to provide conditioning benefits.

Preferably, the hair conditioning agent of the present invention is a siloxane or a siloxane-containing material and is present at a level of from about 0.01% to about 10% of the shampoo composition, preferably from about 0.1% to about 5%, most preferably from about 0.2% to about 3%.

Siloxanes (see, for example, U.S. Pat. No. 3,208,911, Oppliger, issued Sep. 28, 1965) and siloxane-containing polymers have been taught for use in hair conditioning compositions. U.S. Pat. No.4,601,902, Fridd et al., issued Jul. 22, 1986, describes hair conditioning or shampoo/conditioner compositions which include a polydiorganosiloxane having quaternary substituted groups attached to the silicon, and a polydiorganosiloxane having silicon-bonded substituents which are aminosubstituted hydrocarbon groups. U.S. Pat. No. 4,654,161, Kollmeier et al., issued Mar. 31, 1987, describes a group of organopolysiloxanes containing betaine substituents. When used in hair care compositions, these compounds are said to provide good conditioning, compatibility with anionic components, hair substantivity, and low skin irritation. U.S. Pat. No. 4,563,347, Starch, issued Jan. 7, 1986, relates to hair conditioning compositions which include siloxane components containing substituents to provide attachment to hair. Japanese Published Application 56–129,300, Lion Corporation, published Oct. 9, 1981, relates to shampoo conditioner compositions which include an organopolysiloxaneoxyalkylene copolymer together with an acrylic resin. U.S. Pat. No. 4,479,893, Hirota et al., issued Oct. 30, 1984, describes shampoo conditioner compositions containing a phosphate ester surfactant and a silicon derivative (e.g., polyether- or alcoholmodified siloxanes). Polyether-modified polysiloxanes are also disclosed for use in shampoos in U.S. Pat. No. 3,957,970, Korkis, issued May 1976. U.S. Pat. No. 4,185,087, Morlino, issued Jan.

22, 1980, describes quaternary nitrogen derivatives of trialkylamino hydroxy organosilicon compounds which are said to have superior hair conditioning properties.

Siloxane-derived materials have also been used in hair styling compositions. Japanese Published Application 56-092,811, Lion Corporation, published Dec. 27, 1979, describes hair setting compositions which comprise an amphoteric acrylic resin, a polyoxyalkylene-denatured organopolysiloxane, glycol. U.S. Pat. No. 4,744,978, Homan et al., issued May 17, 1988, describes hair styling compositions (such as hair sprays) which include the combination of a carboxyfunctional polydimethylsiloxane and a cationic organic polymer containing amine or ammonium groups. Hair styling compositions which include polydiorganosiloxanes and a cationic organic polymer are taught in U.S. Pat. No. 4,733,677, Gee et al., issued Mar. 29, 1988, and U.S. Pat. No. 4,724,851, Cornwall et al., issued Feb. 16 1988. Finally, European Patent Application 117,360, U.S. Pat. No. 4,760,933, Cantrell et al., published Sep. 5, 1984, discloses compositions, containing a siloxane polymer having at least one nitrogen-hydrogen bond, a surfactant, and a solubilized titanate, zirconate or germanate, which act as both a conditioner and a hair styling aid.

Nonvolatile silicone fluids are useful as the conditioning agent component in the shampoo compositions of the present invention. Examples of such materials include polydimethylsiloxane gums, aminosilicones and phenylsilicones. More specifically, materials such as polyalkyl or polyaryl siloxanes with the following structure:

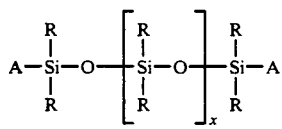

wherein R is alkyl or aryl, and x is an integer from about 7 to about 8,000 may be used. A represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred. Suitable methods for preparing these silicone materials are disclosed in U.S. Pat. Nos. 2,826,551 and 3,964,500 and references cited therein. Silicones useful in the present invention are also commercially available. Suitable examples include Viscasil, a trademark of the General Electric Company and silicones offered by Dow Corning Corporation and by SWS Silicones, a division of Stauffer Chemical Company.

Other useful silicone conditioning materials include materials of the formula:

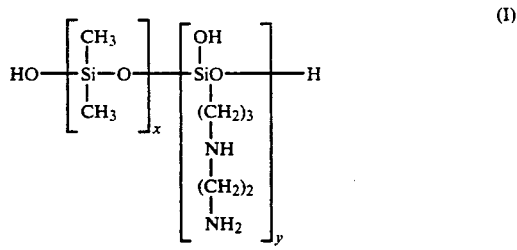

in which x and y are integers which depend on the molecular weight, the average molecular weight being approximately between 5,000 and 10,000. This polymer is also known as "amodimethicone".

Other silicone cationic polymer conditioning agents which can be used in the present compositions correspond to the formula:

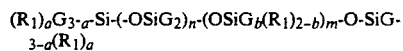

in which G is chosen from the group consisting of hydrogen, phenyl, OH, $C_1$-$C_8$ alkyl and preferably methyl; a denotes 0 or an integer from 1 to 3, and preferably equals 0;

b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10;

$R_1$ is a monovalent radical of formula $C_qH_{2q}L$ in which q is an integer from 2 to 8 and L is chosen from the groups

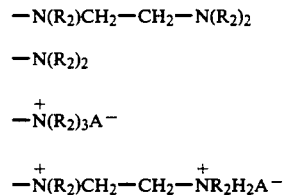

in which $R_2$ is chosen from the group consisting of hydrogen, phenyl, benzyl, a saturated hydrocarbon radical, preferably an alkyl radical containing from 1 to 20 carbon atoms, and $A^-$ denotes a halide ion.

These compounds are described in greater detail in European Patent Application EP 95,238. An especially preferred polymer corresponding to this formula is the polymer known as "trimethylsilylamodimethicone" of formula:

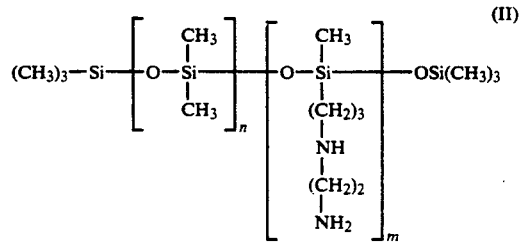

Other silicone cationic polymer conditioning agents which can be used in the present compositions correspond to the formula:

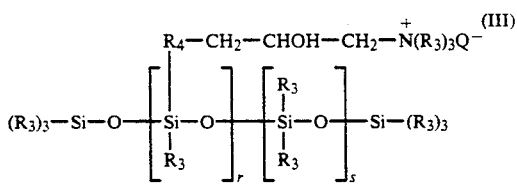

(III)

in which $R_3$ denotes a monovalent hydrocarbon radical having from 1 to 18 carbon atoms, and more especially an alkyl or alkenyl radical such as methyl;

$R_4$ denotes a hydrocarbon radical such as, preferably a $C_1$-$C_{18}$ alkylene radical or a $C_1$-$C_{18}$, and preferably $C_1$-$C_8$, alkyleneoxy radical;

$Q^-$ is a halide ion, preferably chloride;

r denotes an average statistical value from 2 to 20, preferably from 2 to 8;

s denotes an average statistical value from 20 to 200, and preferably from 20 to 50.

These compounds are described in greater detail in U.S. Pat. No. 4,185,017.

A polymer of this class which is especially preferred is that sold by UNION CARBIDE under the name "UCAR SILICONE ALE 56".

Conditioning agent materials also useful in the compositions of the present invention are silicone polymer materials which provide both style retention and conditioning benefits to the hair. These materials comprise rigid silicone polymers.

Some examples of such materials include, but are not limited to, filler reinforced polydimethyl siloxane gums including those having end groups such as hydroxyl; cross linked siloxanes, such as organic substituted silicone elastomers; organic substituted siloxane gums, including those having end groups such as hydroxyl; and resin reinforced siloxanes.

The rigid silicone polymers useful in the present invention have complex viscosities of at least $2 \times 10^5$ poise (P), preferably about $1 \times 10^7$ poise, where complex viscosity is measured by subjecting a sample to oscillatory shear at a fixed frequency of 0.1 rad/sec at 25° C. using a Rheometric Fluids Spectrometer ® measuring films having a thickness of about 1 millimeter. The resulting viscous and elastic force responses are combined to determine the complex modulus which is divided by the imposed frequency to compute the complex viscosity.

A preferred siloxane gum useful in the present invention is a diphenyl-dimethyl polysiloxane gum having a molecular weight of at least about 500,000, and must be diphenyl substituted to the extent of 3% or more, preferably at least about 5%.

The siloxane gums may also be filler reinforced to provide additional rigidity. Silica is the preferred filler. Generally such reinforced gums comprise up to about 15–20% silica.

Silicone resins also useful in formulating the rigid silicones in the present compositions are silicone polymers with a high degree of crosslinking introduced through the use of trifunctional and tetrafunctional silanes. Typical silanes used in the manufacture of resins are monomethyl, dimethyl, monophenyl, diphenyl, methylphenyl, monovinyl, and methylvinyl chlorosilanes, together with tetrachlorosilane. A preferred resin is one offered by General Electric as GE SR545. This resin is provided as a solution in toluene which is stripped prior to the resin's use. This resin is used in combination with the siloxane gum to provide extra rigidity.

Other rigid silicone polymers of use herein are those siloxanes which have been sparingly crosslinked but are still soluble in solvents such as cyclomethicone. Precursors for the rigid material can be any high molecular weight polydimethyl siloxanes, polydimethyl siloxanes containing vinyl groups and other siloxanes. Methods of crosslinking include heat curing with organic peroxides such as dibenzoyl peroxide and di-t-butyl peroxide, heat vulcanization with sulfur, and high-energy radiation.

Obviously, the silicone conditioning agent should be selected such that it does not interfere with the shampoo cleaning and hair style holding performance. Preferably the silicone conditioning agent comprises a polydimethylsiloxane gum, having a viscosity greater than about 1,000,000 centipoise and a dimethicone fluid having a viscosity of from about 10 centipoise to about 100,000 centipoise, wherein the ratio of gum to fluid is from about 30:70 to about 70:30, preferably from about 40:60 to about 60:40.

Alternatively, the hair styling agent and hair conditioning agent of the present compositions can be provided by a single material. Examples of such materials are copolymers having siloxane macromers grafted thereto, which meet the functional limitations as defined supra. That is, the non-silicone backbone of such polymers should have a molecular weight of from about 5,000 to about 1,000,000, a Tg of greater than about −20° C., and a solubility parameter of from about 8.5 to about 12.0.

Preferred polymers comprise a polymeric backbone and, grafted to the backbone, a polydimethylsiloxane macromer having a weight average molecular weight of from about 1,000 to about 50,000, preferably from about 5,000 to about 40,000, most preferably about 10,000. The polymer is such that when it is formulated into the finished hair care composition used to treat the hair, and then the hair dried, the polymer phase separates into a discontinuous phase which includes the polydimethylsiloxane macromer and a continuous phase which includes the backbone It is believed that this phase separation property provides a specific orientation of the polymer on hair which results in the desired hair conditioning and setting benefits.

In its broadest aspect, the copolymers comprise C monomers together with monomers selected from the group consisting of A monomers, B monomers, and mixtures thereof. These copolymers contain at least A or B monomers together with C monomers, and preferred copolymers contain A, B and C monomers.

Examples of useful copolymers and how they are made are described in detail in U.S. Pat. No. 4,693,935, Mazurek, issued Sep. 15, 1987, and U.S. Pat. No. 4,728,571, Clemens et al., issued Mar. 1, 1988, both of which are incorporated herein by reference. These copolymers are comprised of monomers A, C and, optionally, B, which are defined as follows. A, is at least one free radically polymerizable vinyl monomer or monomers. B, when used, comprises at least one monomer copolymerizable with A. When used, B may be up to about 30%, preferably up to about 10%, more preferably 5%, of the total monomers in the copolymer. Monomer C comprises from about 0.01% to about 50.0% of the total monomers in the copolymer.

Representative examples of A monomers are the same as the hydrophobic monomers described supra for the styling polymers of the present invention which do not comprise siloxane macromers.

Representative examples of R monomers are the same as the hydrophilic monomers described supra for the styling polymers of the present invention which do not comprise siloxane macromers.

The C monomer has the general formula:

$$X(Y)_n Si(R)_{3-m} Z_m$$

wherein X is a vinyl group copolymerizable with the A and B monomers; Y is a divalent linking group; R is a hydrogen, lower alkyl, aryl or alkoxy; Z is a monovalent siloxane polymeric moiety having a number average molecular weight of at least about 500, is essentially unreactive under copolymerization conditions and is pendant from the vinyl polymeric backbone, described above; n is 0 or 1; and m is an integer from 1 to 3. C has a weight average molecular weight of from about 1,000 to about 50,000, preferably from about 5,000 to about 40,000, most preferably about 10,000. Preferably, the C monomer has a formula selected from the following group:

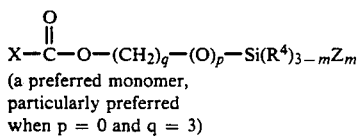

(a preferred monomer, particularly preferred when p = 0 and q = 3)

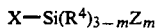

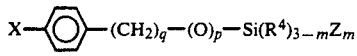

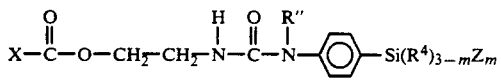

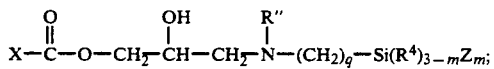

and

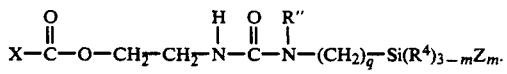

In those structures, m is 1, 2 or 3 (preferably m TM 1); p is or 1; R" is alkyl or hydrogen; q is an integer from 2 to 6; s is an integer from 0 to 2; X is

$R^1$ is hydrogen or —COOH (preferably $R^1$ is hydrogen); $R^2$ is hydrogen, methyl or —CH$_2$COOH (preferably $R^2$ is methyl); Z is

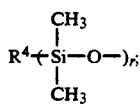

$R^4$ is alkyl, alkoxy, alkylamino, aryl, or hydroxyl (preferably $R^4$ is alkyl); and r is an integer from about 5 to about 700 (peferably r is about 250).

The preferred of these siloxane containing copolymers generally comprise from 50% to about 98% (preferably from about 85% to about 98%, more preferably from about 90% to about 97%) of monomer A, from 0% to about 30% (preferably from about 2% to about 8%) of monomer B, and from about 0.1% to about 50% (preferably from about 0.5% to about 20%, most preferably from about 2% to about 10%) of monomer C. The combination of the A and B monomers preferably comprises from about 50.0% to about 99.9% (more preferably about 80% to about 99%, most preferably from about 90% to about 98%) of the polymer.

Specific polymers which may be used in the present invention include the following (the weight percents below refer to the amount of reactants added in the polymerization reaction, not necessarily the amount in the finished polymer):

--- polyvinyl pyrrolidone/vinyl acetate/polydimethylsiloxane (PDMS) macromer - 10,000 molecular weight (5/90/5 w/w/w) (I)
acrylic acid/n-butylmethacrylate/polydimethylsiloxane (PDMS) macromer - 20,000 molecular weight (10/70/20 w/w/w) (II)
N,N-dimethylacrylamide/isobutyl methacrylate/PDMS macromer - 20,000 molecular weight (20/60/20 w/w/w) (III)
t-butylacrylate/PDMS macromer - 10,000 molecular weight (80/20 w/w) (IV)
t-butylacrylate/N,N - dimethylacrylamide/PDMS macromer - 10,000 molecular weight (70/10/20 w/w/w) (V)
t-butylacrylate/acrylic acid/PDMS macromer - 10,000 molecular weight (75/5/20 w/w/w) (VI).
polyvinyl pyrrolidone/vinyl acetate/polydimethylsiloxane - 20,000 molecular weight (4/95/1 w/w/w) (VII)
polyvinyl pyrrolidone/vinyl acetate/polydimethyl siloxane - 20,000 molecular weight (2.5/95/2.5 w/w/w) (VIII)

---

As with the non-siloxane containing styling polymers described supra, the present copolymers must be diluted with a polymer solvent of the present invention prior to combination with the remaining shampoo composition ingredients. This will enable the formation of a separate dispersed phase of polymer and solvent in the shampoo composition.

When these siloxane-containing copolymers are used in the shampoo compositions of the present invention, to act as both a hair styling polymer and hair conditioning agent, they are generally present at a level of from about 0 2% to about 20%, preferably from about 2% to about 6% .

Most preferably these materials which act as both the hair styling polymer and hair conditioning agent in the present compositions comprise a polyvinyl pyrrolidone/polydimethyl siloxane/vinyl acetate copolymer wherein the non-silicone backbone of the copolymer has a molecular weight of from about 10,000 to about 100,000, a Tg of from about 20° C. to about 60° C., and a solubility parameter, δ, of from about 11.0 to about 11.5.

The hair care compositions herein can contain a variety of other optional components suitable for rendering such compositions more cosmetically or aesthetically acceptable or to provide them with additional usage benefits. Such conventional optional ingredients are well-known to those skilled in the art, e.g., pearlescent aids, such as TiO$_2$ coated mica, ethylene glycol distearate, and PEG 3 distearate; opacifiers; preservatives, such as benzyl alcohol, Glydant, Kathon, methyl paraben, propyl paraben and imidazolidinyl urea; fatty alcohols, such as cetearyl alcohol; sodium chloride; sodium sulfate; polyvinyl alcohol; ethyl alcohol; pH adjusting agents, such as citric acid, sodium citrate, succinic acid, phosphoric acid, monosodium phosphate, disodium phosphate, sodium hydroxide, and sodium carbonate; coloring agents, such as any of the FD&C or D&C dyes; perfumes; sequestering agents, such as disodium ethylenediamine tetra-acetate; and polymer plasticizing agents, such as glycerin and propylene glycol. The present compositions can also optionally comprise thickeners and viscosity modifiers, such as a diethanolamide of a long chain fatty acid (e.g., PEG 3 lauric diethanolamide), lauramide DEA, cocomonoethanol amide, dimethicone copolyols, guar gum, xanthan gum, methyl cellulose, hydroxyethyl cellulose, starches and starch derivatives. The compositions may comprise a nonionic long chain alk.ylated cellulose ether thickener such as those materials described in U.S. Pat. No. 4,228,277, Landoll, issued Oct. 14, 1980, which is incorporated herein by reference. Such optional ingredients generally are used individually at levels of from about 0.01% to about 10.0%, preferably from about 0.05% to about 5.0%, of the shampoo composition.

As with all compositions, the present invention should not contain optional components which unduly interfere with the cleaning and hair style holding performance of the present shampoo compositions.

The balance of the present shampoo compositions comprises water or water combined with some other carrier substance which does not interfere with the cleaning/conditioning/style hold benefits of the present compositions The hair care compositions of the present invention can be made using conventional formulation and mixing techniques The polymer must first be dissolved in the polymer solvent The remaining ingredients are combined in a separate vessel and the polymer/solvent mixture is added. Methods of making various types of hair care compositions are described in the following examples.

Method of Use

The hair care compositions of the present invention are used in conventional ways to provide the hair cleaning/conditioning/ styling hold benefits of the present invention Such method generally involves application of an effective amount of the shampoo product to the hair, which is massaged through and then rinsed from the hair. By "effective amount" is meant an amount sufficient to provide the hair cleaning/conditioning/styling hold benefits desired considering the length and texture of the hair. After the hair is shampooed with the compositions of the present invention, the hair is dried and styled in the usual ways of the user.

The following examples illustrate the present invention. It will be appreciated that other modifications of the present invention within the skill of those in the cosmetic composition formulation art can be undertaken without departing from the spirit and scope of this invention.

All parts, percentages, and ratios herein are by weight unless otherwise specified.

EXAMPLE I

The following is a hair shampoo composition representative of the present invention.

| Component | Weight % |
|---|---|
| Ammonium Lauryl Sulfate | 3.14 |
| Ammonium Laureth Sulfate | 13.56 |
| Cetyl Alcohol | 0.45 |
| Stearyl Alcohol | 0.19 |
| Coco Monoethanol Amide | 3.00 |
| Ethylene Glycol Distearate | 2.00 |
| Tricetyl Methyl Ammonium Chloride | 0.50 |
| Dimethicone | 1.00 |
| Polyvinylpyrrolidone/vinyl acetate (5/95) | 4.00 |
| Phenyl Ethyl Dimethyl Carbinol | 4.00 |
| Perfume | 1.20 |
| Color Solution | 0.25 |
| Kathon | 0.03 |
| Water | 66.68 |

This product is prepared by first dissolving the polyvinylpyrrolidone/vinyl acetate (5/95) copolymer in the phenyl ethyl dimethyl carbinol. The remaining components are combined in a separate vessel with heating and stirring to melt the solids. The polymer/solvent mixture is then added to the remaining components either hot or after they have been cooled.

This shampoo product provides hair cleaning benefits as well as hair conditioning and hair style holding benefits.

EXAMPLE II

The following is a hair shampoo composition representative of the present invention.

| Component | Weight % |
|---|---|
| Ammonium Lauryl Sulfate | 3.00 |
| Ammonium Laureth Sulfate | 10.00 |
| Cetyl Alcohol | 0.19 |
| Stearyl Alcohol | 0.11 |
| Coco Monoethanol Amide | 1.00 |
| Ethylene Glycol Distearate | 2.00 |
| Tricetyl Methyl Ammonium Chloride | 0.50 |
| Polyvinylpyrrolidone/silicone macromer(10k)/ vinyl acetate (5/5/90) | 3.00 |
| Diethyl Phthalate | 4.00 |
| Perfume | 0.8 |
| Color Solution | 0.25 |
| Kathon | 0.03 |
| Water q.s. to | 100% |

This product is prepared using the method described in Example I.

This shampoo product provides hair cleaning benefits as well as hair conditioning and hair style holding benefits.

EXAMPLE III

The following is a hair shampoo composition representative of the present invention.

| Component | Weight % |
|---|---|
| Cocoamidopropyl Betaine | 12.52 |
| Sodium Cocoamphoglycinate | 4.18 |
| Coco Methanol Amide | 1.50 |
| Ethylene Glycol Distearate | 1.50 |
| Ticetyl Methyl Ammonium Chloride | 0.50 |
| Dimethicone | 3.00 |
| Polyvinyl Pyrrolidone/Vinyl Acetate (10/90) | 5.00 |
| Phenyl Ethyl Dimethyl Carbinol | 6.00 |
| Perfume | 1.20 |
| Color Solution | 0.25 |
| Kathon | 0.03 |

-continued

| Component | Weight % |
|---|---|
| Water q.s. to | 100% |

This product is prepared using the method described in Example I.

This shampoo product provides hair cleaning benefits as well as hair conditioning and hair style holding benefits.

EXAMPLE IV

The following is a hair shampoo composition representative of the present invention.

| Component | Weight % |
|---|---|
| Cocoamidopropyl Betaine | 8.30 |
| Ammonium Laureth Sulfate | 6.30 |
| Ammonium Lauryl Sulfate | 2.10 |
| Coco Monoethanol Amide | 1.50 |
| Hydroxypropyl Methocellulose (K15) | 0.25 |
| Ethylene Glycol Distearate | 1.50 |
| Tricetyl Methyl Ammonium Chloride | 0.50 |
| Polyvinyl Pyrrolidone/Vinyl Acetate (5/95) | 6.00 |
| Ethyl-6-Acetoxy Hexanoate | 6.00 |
| Perfume | 1.20 |
| Color Solution | 0.25 |
| Kathon | 0.03 |
| Water q.s. to | 100% |

This product is prepared using the method described in Example I.

This shampoo product provides hair cleaning benefits as well as hair conditioning and hair style holding benefits.

EXAMPLE V

The following is a hair shampoo composition representative of the present invention.

| Component | Weight % |
|---|---|
| Cocomidopropyl Betaine | 9.00 |
| Sodium Lauroyl Sarcosinate | 4.40 |
| Ammonium Lauryl Sulfate | 3.00 |
| Coco Monoethanol Amide | 1.50 |
| Hydroxypropyl Methocellulose (K15) | 0.25 |
| Ethylene Glycol Distearate | 1.50 |
| Tricetyl Methyl Ammonium Chloride | 0.50 |
| Dimethicone | 1.00 |
| Poly t-Butyl Acrylate (MW = 100,000) | 4.00 |
| Ethyl-6-Acetoxy Hexanoate | 4.00 |
| Perfume | 1.20 |
| Color Solution | 0.25 |
| Kathon | 0.03 |
| Water q.s. to | 100% |

This product is prepared using the method described in Example I.

This shampoo product provides hair cleaning benefits as well as hair conditioning and hair style holding benefits.

What is claimed is:

1. A hair shampoo composition comprising:
   a. from about 5% to about 30% of a surfactant;
   b. from about 0.2% to about 20% of a hair styling polymer comprising:
      A. from 0% to about 30% of a polymerizable hydrophilic monomer ($M_A$), or mixtures thereof; and
      B. from about 70% to about 100% of a polymerizable hydrophobic monomer ($M_B$), or mixtures thereof;
      said polymer having a weight average molecular weight of from about 5,000 to about 1,000,000, a Tg of greater than about $-20°$ C., and a solubility parameter, $\delta$, of from about 8.5 to about 12.0; and
   c. from about 0.2% to about 20% of a solvent which will solubilize said polymer, said solvent having a boiling point of less than or equal to about 300° C., and a solubility parameter, $\delta_s$, of from about 7 to about 12.5; and wherein the polymer and solvent are present in the hair shampoo composition as a dispersed fluid phase; wherein the ratio of polymer to solvent is from about 20:80 to about 80:20; and wherein the percent hydrophilic monomer, $M_A$, is present, is as follows:

$$\% M_A = (\delta_s - 6.7) \times 5.56 \pm 10$$

2. The shampoo composition of claim 1 wherein $\delta$ is from about 9.5 to about 11.5.

3. The shampoo composition of claim 2 wherein $\delta$ is from about 11 to about 11.5.

4. The shampoo composition of claim 3 wherein the hydrophobic monomer is selected from the group consisting of acrylic acid esters of $C_1-C_{18}$ alcohols; methacrylic acid esters of $C_1-C_{18}$ alcohols; styrene; polystyrene macromer; vinyl acetate; vinyl chloride; vinylidene chloride; vinyl propionate; alpha-methylstyrene; t-butylstyrene; butadiene; cyclohexadiene; ethylene; propylene; vinyl toluene; methoxy ethyl methacrylate; and mixtures thereof.

5. The shampoo composition of claim 3 wherein the percent hydrophilic monomer is as follows:

$$\% M_A = (\delta_s - 6.7) \times 5.56 \pm 3.$$

6. The shampoo composition of claim 3 wherein the hair styling polymer comprises both the polymerizable hydrophilic monomer and the polymerizable hydrophobic monomer.

7. The shampoo composition of claim 6 wherein the hydrophilic monomer is selected from the group consisting of acrylic acid, methacrylic acid, N,N-dimethylacrylamide, dimethylaminoethyl methacrylate, methacrylamide, N-t-butyl acrylamide, maleic acid, maleic anhydride, half esters of maleic anhydride, crotonic acid, itaconic acid, acrylamide, acrylate alcohols, hydroxyethyl methacrylate, vinyl pyrrolidone, vinyl ethers, maleimides, vinyl pyridine, vinyl imidazole, styrene sulfonate, allyl alcohol, vinyl alcohol, vinyl caprolactam, and mixtures thereof.

8. The shampoo composition of claim 7 wherein the hydrophobic monomer is selected from the group consisting of acrylic acid esters of $C_1-C_{18}$ alcohols; methacrylic acid esters of $C_1-C_{18}$ alcohols; styrene; polystyrene macromer; vinyl acetate; vinyl chloride; vinylidene chloride; vinyl propionate; alphamethylstyrene; t-butylstyrene; butadiene; cyclohexadiene; ethylene; propylene; vinyl toluene; methoxy ethyl methacrylate; and mixtures thereof.

9. The shampoo composition of claim 1 wherein the hair styling polymer is selected from the group consisting of vinyl pyrrolidone/vinyl acetate copolymer; t-butyl acrylate homopolymer; t-butyl styrene/ethyl hexyl methacrylate copolymer (50/50); dimethyl acrylamide/t-butyl acrylate/ethyl hexyl methacrylate copolymer (10/45/45); ethylene/vinyl acetate copolymer (12.5/87.5); styrene/allyl alcohol copolymer (81/19); vinyl chloride vinyl acetate copolymer (83/17 and lower); vinyl pyrrolidone/vinyl acetate/butyl acrylate copolymer (10/78/12 and 10/70/20); vinyl pyrrolidone/vinyl acetate/butyl acrylate/styrene sulfonate copolymer (10/70/17/5); vinyl pyrrolidone/vinyl propionate copolymer (5/95); vinyl caprolactam/vinyl acetate copolymer (5/95); ethyl acrylate/acrylic acid/N-t-butyl acrylamide copolymer; vinyl acetate/crotonic acid copolymer 90/10; vinyl acetate/vinyl propionate/crotonic acid 50/40/10; vinyl acetate/vinyl neodecanoate/crotonic acid copolymer; and mixtures thereof.

10. The shampoo composition of claim 1 wherein the hair styling polymer is present in the composition at a level of from about 2% to about 6%.

11. The shampoo composition of claim 10 wherein the hair styling polymer is a vinyl pyrrolidone/vinyl acetate copolymer.

12. The shampoo composition of claim 11 wherein the vinyl pyrrolidone/vinyl acetate copolymer has a monomer weight ratio of 5/95.

13. The shampoo composition of claim 1 wherein $\delta_s$ is from about 8 to about 10.

14. The shampoo composition of claim 13 wherein the level of solvent is from about 2% to about 6%.

15. The shampoo composition of claim 14 wherein the solvent for the hair styling polymer is selected from the group consisting of iso-propanol, butyl alcohol, amyl alcohol, phenyl ethanol, benzyl alcohol, phenyl propanol, ethyl butyrate, iso-propyl butyrate, diethyl phthalate, phenyl ethyl dimethyl carbinol, ethyl-6-acetoxyhexanoate, methyl (2-pentanyl-3-oxy) cyclopentyl acetate, and mixtures thereof.

16. The shampoo composition of claim 15 wherein the ratio of polymer to solvent is from about 40:60 to about 60:40.

17. The shampoo composition of claim 11 wherein the solvent for the hair styling polymer is selected from the group consisting of diethyl phthalate, phenyl ethyl dimethyl carbinol, ethyl-6-acetoxyhexanoate, and mixtures thereof.

18. The shampoo composition of claim 1 wherein the surfactant is selected from anionic, nonionic, cationic, zwitterionic amphoteric surfactants, and mixtures thereof.

19. The shampoo composition of claim 18 wherein the surfactant is selected from the group consisting of anionic surfactants, zwitterionic surfactants, amphoteric surfactants and mixtures thereof.

20. The shampoo composition of claim 19 wherein the surfactant is at a level of from about 12% to about 25% in the composition.

21. The shampoo composition of claim 20 wherein the surfactant comprises alkyl sulfates, ethoxylated alkyl sulfates, and mixtures thereof.

22. The shampoo composition of claim 21 wherein the surfactant additionally comprises a surfactant selected from the group consisting of betaines, amido propyl betaines, sarcosinates, cocoamphocarboxy glycinate, and mixtures thereof.

23. The shampoo composition of claim 20 wherein the surfactant is selected from the group consisting of ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauroyl sulfate, triethanolamine lauroyl sulfate, triethanolamine lauroyl sulfate, sodium tridecyl benzene sulfonate, sodium dodecyl benzene sulfonate, cocobetaine, oleyl betaine, cocoamido-propyl betaine, lauryl amido propyl betaine, cocoamphocarboxy glycinate, sodium lauroyl sarcosinate, and mixtures thereof.

24. The shampoo composition of claim 1 additionally comprising a silicone conditioning agent, which is present in the shampoo composition as a separate dispersed phase.

25. The shampoo composition of claim 24 wherein the silicone conditioning agent is present at a level of from about 0.01% to about 10%.

26. The shampoo composition of claim 25 wherein the silicone conditioning agent is present at a level of from about 0.1% to about 5% and comprises a polydimethyl siloxane gum having a viscosity at 25° C. greater than about 1,000,000 centipoise, and a dimethicone fluid having a viscosity at 25° C. of from about 10 centipoise to about 100,000 centipoise, wherein the ratio of gum to fluid is from about 30:70 to about 70:30.

27. The shampoo composition of claim 24 wherein the silicone conditioning agent comprises a siloxane macromer grafted to the hair styling polymer.

28. The shampoo composition of claim 27 wherein the hair styling polymer is selected from the group consisting of vinyl pyrrolidone/polydimethyl siloxane/vinyl acetate copolymers.

29. The shampoo composition of claim 28 wherein the hair styling polymer comprises a vinyl pyrrolidone/polydimethyl siloxane/vinyl acetate copolymer (5/5/90).

30. A hair shampoo composition comprising:
 a. from about 12% to about 25% of a surfactant comprising alkyl sulfates, ethoxylated alkyl sulfates and cocoamidopropyl betaine;
 b. from about 2% to about 6% of a hair styling polymer selected from polyvinyl pyrrolidone/vinyl acetate copolymers, having a weight average molecular weight of from about 10,000 to about 100,000, a Tg of from about 20° C. to about 60° C., and a solubility parameter, $\delta$, of from about 11 to about 11.5; and
 c. from about 2% to about 6% of a solvent which will solubilize said polymer selected from the group consisting of diethyl phthalate, phenylethyldimthylcarbinol, ethyl-6-acetoxy hexanoate, and mixtures thereof;
wherein the polymer and solvent are present in the shampoo composition as a dispersed fluid phase, the ratio of polymer to solvent is from about 40:60 to about 60:40, and the percent vinyl pyrrolidone in the copolymer is equal to $(\delta_s - 6.7) \times 5.56 \pm 3$, where $\delta_s$ is the solubility parameter of the solvent for the polymer.

31. A hair shampoo composition comprising:
 a. from about 12% to about 25% of a surfactant comprising alkyl sulfates, ethoxylated alkyl sulfates, and cocoamido propyl betaine;

b. from about 2% to about 6% of a hair styling polymer selected from t-butyl acrylate homopolymers, having a weight average molecular weight of from about 10,000 to about 100,00, a Tg of from about 20° C. to about 60° C., and c. from about 2% to about 6% of a solvent which will solubilize said polymer selected from the group consisting of diethyl phthalate, phenylethyldimthylcarbinol, ethyl-6-acetoxy hexanoate, and mixtures thereof;

wherein the polymer and solvent are present in the shampoo composition as a dispersed fluid phase, the ratio of polymer to solvent is from about 40:60 to about 60:40.

32. A hair shampoo composition comprising:

a. from about 15% to about 20% of surfactant which comprises from about 2% to 10% cocoamidopropyl betaine, from about 2% to about 6% alkyl sulfate, from 0% to about 14% ethoxylated alkyl sulfate, and from 0% to about 8% of lauroyl sarcosinate;

b. from about 2% to about 6% of a hair styling polymer selected from polyvinyl pyrrolidone/vinyl acetate copolymers, having a weight average molecular weight of from about 10,000 to about 100,000, Tg of from about 20° C. to about 60° C., and a solubility parameter, δ, of from about 11 to about 11.5; and c. from about 2% to about 6% of a solvent which will solubilize said polymer selected from the group consisting of diethyl phthalate, phenethyl dimethyl carbinol, ethyl-6-acetoxy hexanoate, and mixtures thereof;

wherein the polymer and solvent are present in the shampoo composition as a dispersed fluid phase, the ratio of polymer to solvent is from about 40:60 to about 60:40, and the percent vinyl pyrrolidone in the copolymer is equal to $(\delta_s - 6.7) \times 5.56 \pm 3$, where $\delta_s$ is the solubility parameter of the solvent for the polymer.

33. The shampoo composition of claim 30 additionally comprising from about 0.2% to about 3% of a silicone conditioning agent which comprises a polydimethyl siloxane gum having a viscosity at 25° C. greater than about 1,000,000 centipoise and a dimethicone fluid having a viscosity at 25° C. of between about 10 centipoise and about 100,000 centipoise, wherein the ratio of gum to fluid is from about 40:60 to about 60:40.

34. The shampoo composition of claim 31 additionally comprising from about 0.2% to about 3% of a silicone conditioning agent which comprises a polydimethyl siloxane gum having a viscosity at 25° C. greater than about 1,000,000 centipoise and a dimethicone fluid having a viscosity at 25° C. of between about 10 centipoise and about 100,000 centipoise, wherein the ratio of gum to fluid is from about 40:60 to about 60:40.

35. The shampoo composition of claim 32 additionally comprising from about 0.2% to about 3% of a silicone conditioning agent which comprises a polydimethyl siloxane gum having a viscosity at 25° C. greater than about 1,000,000 centipoise and a dimethicone fluid having a viscosity at 25° C. of between about 10 centipoise and about 100,000 centipoise, wherein the ratio of gum to fluid is from about 40:60 to about 60:40.

36. A hair shampoo composition comprising:

a. from about 12% to about 25% of a surfactant comprising alkyl sulfates, ethoxylated alkyl sulfates, and cocoamidopropyl betaine;

b. from about 2% to about 6% of a hair styling polymer which comprises a polyvinyl pyrrolidone/polydimethyl siloxane/vinyl acetate copolymer, having a weight average molecular weight of from about 10,000 to about 100,000, a Tg of from about 20° C. to about 60° C., and a solubility parameter, δ, of from about 11.0 to about 11.5; and c. from about 2% to about 6% of a solvent which will solubilize said polymer selected from the group consisting of diethyl phthalate, phenyl ethyl dimethyl carbinol, ethyl-6-acetoxy hexanoate, and mixtures thereof;

wherein the polymer and solvent are present in the shampoo composition as a dispersed fluid phase; the ratio of polymer to solvent si from about 40:60 to about 60:40; and the percent vinyl pyrrolidone in the copolymer is equal to $(\delta_s - 6.7) \times 5.56 \pm 3$, where $\delta_s$ is the solubility parameter of the solvent for the polymer.

37. A method for providing styling hold to hair, said method comprising shampooing the hair with the shampoo composition of claim 1.

38. A method for providing conditioning and styling hold to hair, said method comprising shampooing the hair with the shampoo composition of claim 33.

39. A method for providing conditioning and styling hold to hair, said method comprising shampooing the hair with the shampoo composition of claim 34.

40. A method for providing conditioning and styling hold to hair, said method comprising shampooing the hair with the shampoo composition of claim 35.

41. A method for providing conditioning and styling hold to hair, said method comprising shampooing the hair with the shampoo composition of claim 36.

* * * * *

UNITED STATES PATENT AND TRADEMARK OFFICE
CERTIFICATE OF CORRECTION

PATENT NO. : 5,120,532
DATED : June 9, 1992
INVENTOR(S) : R. L. Wells, B.T. KING, M.A. Synder, D. H. Frey It is certified that error appears in the above-indentified patent and that said Letters Patent is hereby corrected as shown below:

On the title page: Item [54]

In the title "Hair Styling Shampoos" should read--Hair Styling Shampoos Containing Hair Styling Polymers and Solvents Within Particular Solubility Parameter Ranges--

Column 1 in the title "Hair Styling Shampoos" should read--Hair Styling Shampoos Containing Hair Styling Polymers and Solvents Within Particular Solubility Parameter Ranges--

Column 3, line 23 "infra. in" should read--infra, in--

Column 4, line 12 "a alcohols" should read--alcohols--

Column 4, line 20 "3,5,5-trimethyl 1-hexanol" should read--3,5,5-trimethyl-1-hexanol--

Column 4, line 59 "Ultrahold CA 8" should read--Ultrahold 8--

Column 8, line 9 "f" should read--of--

Column 10, line 61 "*Technology.*" should read--*Technology,*--

UNITED STATES PATENT AND TRADEMARK OFFICE
CERTIFICATE OF CORRECTION

PATENT NO. : 5,120,532     Page 2 of 2
DATED : June 9, 1992
INVENTOR(S) : R. L. Wells, B. T. King, M. A. Snyder, D. H. Frey It is certified that error appears in the above-identified patent and that said Letters Patent is hereby corrected as shown below:

Column 12, line 67 "3-(P,P-dimethyl-P-dodecylphosphonio]" should read --3-[P,P-dimethyl-P-dodecylphosphonio]--

Column 15, line 9 "glycol" should read --and polyethylene glycol--

Column 19, line 5 "R" should read --B--

Column 19, line 51 "m TM 1" should read --m = 1--

Column 20, line 3 "peferably" should read --preferably --.

Column 20, line 49 "0 2%" should read --0.2%--

Column 21, line 18 "alk.ylated" should read --alkylated--

Column 22, Example III "Kathon" should read --Kathan--

Column 25, line 4 "chloride vinyl" should read --chloride/vinyl--

Column 26, line 56 "phenylethyldim-" should read --phenylethyldiem--

Signed and Sealed this

Seventh Day of January, 1997

BRUCE LEHMAN

Attest:

Attesting Officer     Commissioner of Patents and Trademarks